(12) United States Patent
St. Cyr et al.

(10) Patent No.: US 9,927,335 B2
(45) Date of Patent: *Mar. 27, 2018

(54) SAMPLE HOLDERS AND METHODS OF USING THEM

(71) Applicant: PERKINELMER HEALTH SCIENCES, INC., Waltham, MA (US)

(72) Inventors: Paul L St. Cyr, Shelton, CT (US); Michael L. DelVecchio, Stratford, CT (US); Leonard J. Weisgable, Oxford, CT (US); John T. Buturla, Fairfield, CT (US); Stephen M Pignataro, Norwalk, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/197,194

(22) Filed: Jun. 29, 2016

(65) Prior Publication Data

US 2017/0045425 A1     Feb. 16, 2017

Related U.S. Application Data

(63) Continuation of application No. 13/662,500, filed on Oct. 28, 2012, now Pat. No. 9,412,572.

(51) Int. Cl.
*G01N 1/36* (2006.01)
*H01J 49/04* (2006.01)
*B01L 9/00* (2006.01)
*G01N 1/28* (2006.01)

(52) U.S. Cl.
CPC ............ *G01N 1/36* (2013.01); *B01L 9/50* (2013.01); *B01L 9/52* (2013.01); *G01N 1/28* (2013.01); *H01J 49/0409* (2013.01); *B01L 2200/025* (2013.01); *B01L 2300/043* (2013.01); *B01L 2300/0681* (2013.01); *B01L 2300/0829* (2013.01); *G01N 2001/368* (2013.01)

(58) Field of Classification Search
CPC ........................... G01N 1/36; G01N 2001/368
See application file for complete search history.

(56) References Cited

U.S. PATENT DOCUMENTS

| 4,153,178 A * | 5/1979 | Weavers ............ E05C 1/04 206/387.1 |
| 9,412,572 B2 * | 8/2016 | St Cyr ............ H01J 49/0409 |
| 2011/0129929 A1 * | 6/2011 | Day ............ G01N 9/002 436/8 |

\* cited by examiner

*Primary Examiner* — Paul West
(74) *Attorney, Agent, or Firm* — Rhodes IP PLC; Christopher R Rhodes

(57) ABSTRACT

Certain embodiments described herein are directed to sample holders that can be used to retain a sample support effective for use in direct sample analysis. In some embodiments, the sample support can include a first and a second plate with apertures to permit a sample to be analyzed using direct sample analysis.

15 Claims, 11 Drawing Sheets

SAMPLE HOLDERS AND METHODS OF USING THEM

TECHNOLOGICAL FIELD

Certain features, aspects and embodiments are directed to sample holders and methods of using them. In certain examples, the sample holders can be configured for use in direct sample analysis.

BACKGROUND

Direct sample analysis permits analysis of a sample by directly introducing the sample into an instrument. If desired, front-end chromatography separation can be omitted prior to analysis of the sample.

SUMMARY

Certain features, aspects and embodiments described herein are directed to sample holders that can be used to hold or retain a sample support to permit direct sample analysis of a sample on the sample support. The exact configuration of the sample holder may vary, and illustrations of different types of sample holders are described in detail below.

In one aspect, a sample holder comprising a first plate comprising at least one aperture to permit a sample on a sample support to be contacted by fluid for direct sample analysis, the first plate comprising a retaining device is provided. In some embodiments, the sample holder can also comprise a second plate rotatably coupled to the first plate and comprising a corresponding aperture to the at least one aperture of the first plate, the second plate configured to rotate to engage the first plate and retain the sample support between the first plate and the second plate, in which the retaining device of the first plate is configured to engage the second plate to the first plate in a first position to retain the sample support between the first plate and the second plate and to disengage the second plate from the first plate in a second position to permit removal of the sample support from the sample holder.

In certain examples, each of the first plate and the second plate comprise a plurality of apertures to permit sample loading on the sample support. In other examples, the first plate and second plate are configured to permit contact of the sample by fluid at one side of the sample holder to ionize sample on the sample support. In some embodiments, the first plate and second plate are configured to permit flow of the ionized sample from a second side of the sample holder. In some examples, the retaining device of the first plate is configured to slide laterally to engage the second plate in the first position and disengage the second plate in the second position. In other embodiments, the retaining device comprises two sliding devices each configured to slide laterally to disengage the first plate from the second plate and to slide medially to engage the first plate to the second plate. In further embodiments, the first plate and the second plate are asymmetric. In other embodiments, the first plate and the second plate each comprise an effective material to permit contact of sample on the sample support by a plasma without substantial degradation of the first plate and the second plate. In additional embodiments, each of the first plate and the second plate comprises stainless steel. In some embodiments, at least one of the first plate and the second plate comprises a plastic. In certain examples, the plastic is polyetheretherketone. In further examples, each of the first plate and the second plate comprise the same number of apertures. In additional embodiments, the apertures of the first plate and the second plate comprise the same geometry. In some examples, the geometry is circular. In certain embodiments, the circular apertures have a center-to-center spacing of about 0.2 inches to about 0.75 inches, e.g., about 0.5 inches. In certain examples, at least one of the first plate and the second plate comprises an alignment mechanism for receiving the sample support. In further embodiments, one of the first plate and the second plate comprises a ball and the other plate comprises a socket. In some embodiments, the first plate and second plate are coupled to each other through a hinge. In further examples, the first plate comprises a different number of apertures than the second plate. In additional examples, the sample holder is configured to retain the sample support between the first plate and the second plate in the first position of the retaining device without the use of an external fastener.

In another aspect, a sample holder configured to retain a sample support for direct sample analysis of a sample on the sample support, the sample holder comprising a first plate coupled to a second plate through at least one joint, the first plate comprising a sliding device configured to hold the second plate towards the first plate in a first position and to permit rotation of the second plate away from the first plate in the second position, in which the holding of the second plate towards the first plate is effective to retain the sample support between the first plate and the second plate is provided.

In certain embodiments, each of the first plate and the second plate comprise a plurality of apertures to permit sample loading on the sample support. In other embodiments, the first plate and second plate are configured to permit contact of the sample by fluid at one side of the sample holder to ionize sample on the sample support. In additional embodiments, the first and second plates are configured to permit flow of the ionized sample from a second side of the sample holder. In further embodiments, the sliding device comprises two sliding devices each configured to slide laterally to disengage the first plate from the second plate and to slide medially to engage the first plate to the second plate. In some examples, the sliding device comprises a single sliding device configured to slide laterally to disengage the first plate from the second plate and to slide medially to engage the first plate to the second plate. In some embodiments, the first plate and the second plate are asymmetric. In further embodiments, the first plate and the second plate each comprise an effective material to permit contact of sample on the sample support by a plasma without substantial degradation of the first plate and the second plate. In other embodiments, each of the first plate and the second plate comprises stainless steel. In additional examples, at least one of the first plate and the second plate comprises a plastic. In some embodiments, the plastic is polyetheretherketone. In other embodiments, each of the first plate and the second plate comprise the same number of apertures. In additional embodiments, the apertures of the first plate and the second plate comprise the same geometry. In certain examples, the geometry is circular. In some embodiments, the circular apertures have a center-to-center spacing of about 0.25 to about 0.75 inches, e.g., about 0.5 inches. In some embodiments, at least one of the first plate and the second plate comprises an alignment mechanism for receiving the sample support. In further embodiments, the joint is configured as a ball-and-socket joint. In certain examples, the joint is configured as a hinge joint. In some examples, the first plate comprises a different number of apertures than the second plate. In further examples, the sample holder is configured to bias the second plate toward the first plate without the use of an external fastener.

In an additional aspect, a sample holder for direct sample analysis, the sample holder comprising a first plate comprising at least one aperture to permit a sample on a sample support to be contacted by fluid for direct sample analysis, the first plate comprising a retaining device is described. In certain embodiments, the holder can comprise a second plate comprising an integral sample support and configured to removably couple to the first plate, the second plate further configured to rotate to engage the first plate, in which the retaining device of the first plate is configured to engage the second plate to the first plate in a first position and to disengage the second plate from the first plate in a second position.

In certain examples, each of the first plate and the second plate comprise a plurality of apertures to permit sample analysis of samples on the sample support. In other examples, the first plate and second plate are configured to permit contact of the sample by fluid at one side of the sample holder to ionize sample on the sample support. In some embodiments, the first plate and second plate are configured to permit flow of the ionized sample from a second side of the sample holder. In other embodiments, the retaining device of the first plate is configured to slide laterally to engage the first plate in the first position and disengage the first plate in the second position. In further embodiments, the retaining device comprises two sliding devices each configured to slide laterally to disengage the first plate from the second plate and to slide medially to engage the first plate to the second plate. In certain examples, the first plate and the second plate are asymmetric. In some embodiments, the first plate and the second plate each comprise an effective material to permit contact of sample on the sample support by a plasma without substantial degradation of the first plate and the second plate. In certain examples, each of the first plate and the second plate comprises stainless steel. In additional examples, at least one of the first plate and the second plate comprises a plastic. In some embodiments, the plastic is polyetheretherketone. In other examples, each of the first plate and the second plate comprise the same number of apertures. In certain embodiments, the apertures of the first plate and the second plate comprise the same geometry. In some examples, the geometry is circular. In additional examples, the circular apertures have a center-to-center spacing of about 0.25 inches to about 0.75 inches, e.g., about 0.5 inches. In other embodiments, at least one of the first plate and the second plate comprises an alignment mechanism for receiving the sample support. In some examples, one of the first plate and the second plate comprises a ball and the other plate comprises a socket. In certain embodiments, the first plate and the second plate are coupled to each other through a hinge. In some examples, the first plate comprises a different number of apertures than the second plate. In some embodiments, the sample holder is configured to retain the sample support between the first plate and the second plate in the first position of the retaining device without the use of an external fastener.

In another aspect, a kit comprising a first plate comprising at least one aperture to permit a sample on a sample support to be contacted by fluid for direct sample analysis, the first plate comprising a retaining device, and a second plate configured to removably couple to the first plate, the second plate configured, when coupled to the first plate, to rotate to engage the second plate to the first plate and retain the sample support between the first plate and the second plate, in which the retaining device of the first plate is configured to engage the second plate in a first position to retain the sample support between the first plate and the second plate and is configured to disengage the second plate in a second position to permit removal of the sample support from the sample holder is provided.

In certain embodiments, the kit can include at least one sample support. In some examples, the sample support comprises a mesh. In other examples, the sample support is positioned in a housing. In some embodiments, the housing of the sample support is configured for insertion between the first plate and the second plate. In other examples, the kit can comprise an additional second plate comprising a different number of apertures than the second plate. In some examples, the kit can comprise an additional first plate comprising a different number of apertures than the first plate. In certain examples, the kit can comprise an additional second plate comprising an aperture sized differently than an aperture of the second plate. In other examples, the kit can comprise an additional first plate comprising an aperture sized differently than the at least one aperture of the first plate. In further examples, the kit can comprise a plurality of sample supports, in which at least two of the sample supports are different from each other.

In an additional aspect, a method of loading a sample for direct sample analysis is disclosed. In certain examples, the method comprises providing a sample holder comprising a first plate comprising at least one aperture to permit a sample on a sample support to be contacted by fluid for direct sample analysis, the first plate comprising a retaining device, and a second plate rotatably coupled to the first plate and comprising a corresponding aperture to the at least one aperture of the first plate, the second plate configured to rotate to engage the first plate and retain the sample support between the first plate and the second plate, in which the retaining device of the first plate engages the second plate in a first position to retain the sample support between the first plate and the second plate and disengages the second plate in a second position to permit removal of the sample support from the sample holder.

In certain embodiments, the method comprises providing instructions for loading the sample on the sample support. In other embodiments, the method comprises providing instructions for inserting the sample support into the sample holder. In some embodiments, the method comprises providing a sample support. In certain embodiments, the method comprises providing instructions for analyzing the sample on the sample support using direct sample analysis.

In another aspect, a method of loading a sample for direct sample analysis comprising providing a sample holder configured to retain a sample support for direct sample analysis of a sample on the sample support, the sample holder comprising a first plate attached to a second plate through at least one joint, the first plate comprising a sliding device configured to hold the second plate towards the first plate in a first position and to permit rotation of the second plate away from the first plate in the second position, in which the holding of the second plate towards the first plate retains the sample support between the first plate and the second plate is disclosed.

In certain embodiments, the method comprises providing instructions for loading the sample on the sample support. In some embodiments, the method comprises providing instructions for inserting the sample support into the sample holder. In certain examples, the method comprises providing a sample support. In certain embodiments, the method comprises providing instructions for analyzing the sample on the sample support using direct sample analysis.

In an additional aspect, a method of loading a sample for direct sample analysis comprising providing a sample holder comprising a first plate comprising at least one aperture to permit a sample on a sample support to be contacted by fluid for direct sample analysis, the first plate comprising a retaining device, and a second plate comprising an integral sample support and configured to removably couple to the first plate, the second plate further configured to rotate to engage the first plate, in which the retaining device of the first plate is configured to engage the second plate to the first plate in a first position and to disengage the second plate from the first plate in a second position is described.

In certain examples, the method comprises providing instructions for loading the sample on the sample support. In other examples, the method comprises providing instructions for inserting the sample support into the sample holder. In some examples, the method comprises providing a sample support. In certain examples, the method comprises providing instructions for analyzing the sample on the sample support using direct sample analysis.

Other aspects and attributes will become apparent to those skilled in the art after review of the detailed description and accompanying drawings.

BRIEF DESCRIPTION OF FIGURES

Certain configurations are provided below for illustrative purposes only with reference to the accompanying figures in which.

Additional features, aspects and embodiments are described in more detail below. It will be recognized by the person of ordinary skill in the art, given the benefit of this disclosure, that the lengths and dimensions shown in the figures are not limiting and that many different lengths and dimensions can be used depending on the size of the sample support, the system which the sample holder is to be used in and other factors.

DETAILED DESCRIPTION

Certain embodiments of sample holders are described below. The exact configuration of the sample holders including, for example, the length and width of the plates, size and configuration of the apertures or openings, materials used in the plates and the like can vary depending on the particular instrument the sample holder is to be used in and/or depending on the nature of the sample to be analyzed. Where direct sample analysis is referred to below, no particular configuration of a direct sample analysis device or system is intended to be required as being necessary for properly using the sample holder. For illustration purposes, some configurations of a direct sample analysis device or system are described herein. The term "plate" is used for convenience purposes to refer to certain components of the sample holders described herein. The plates of the sample holders can be any device comprising a surface that is configured to engage to another surface and retain a sample support between the surfaces. If desired, the surfaces may contact the sample support in one or more areas to prevent movement of the sample support during analysis. In some examples, the plates contact substantially the same surface area of the sample support, whereas in other configurations, different plates physically contact a different amount of surface area of the sample support. In some configurations described herein, the plates of the sample holders are generally planar structures that can position a sample support between substantially parallel surfaces of the planar structures.

Figure 1:
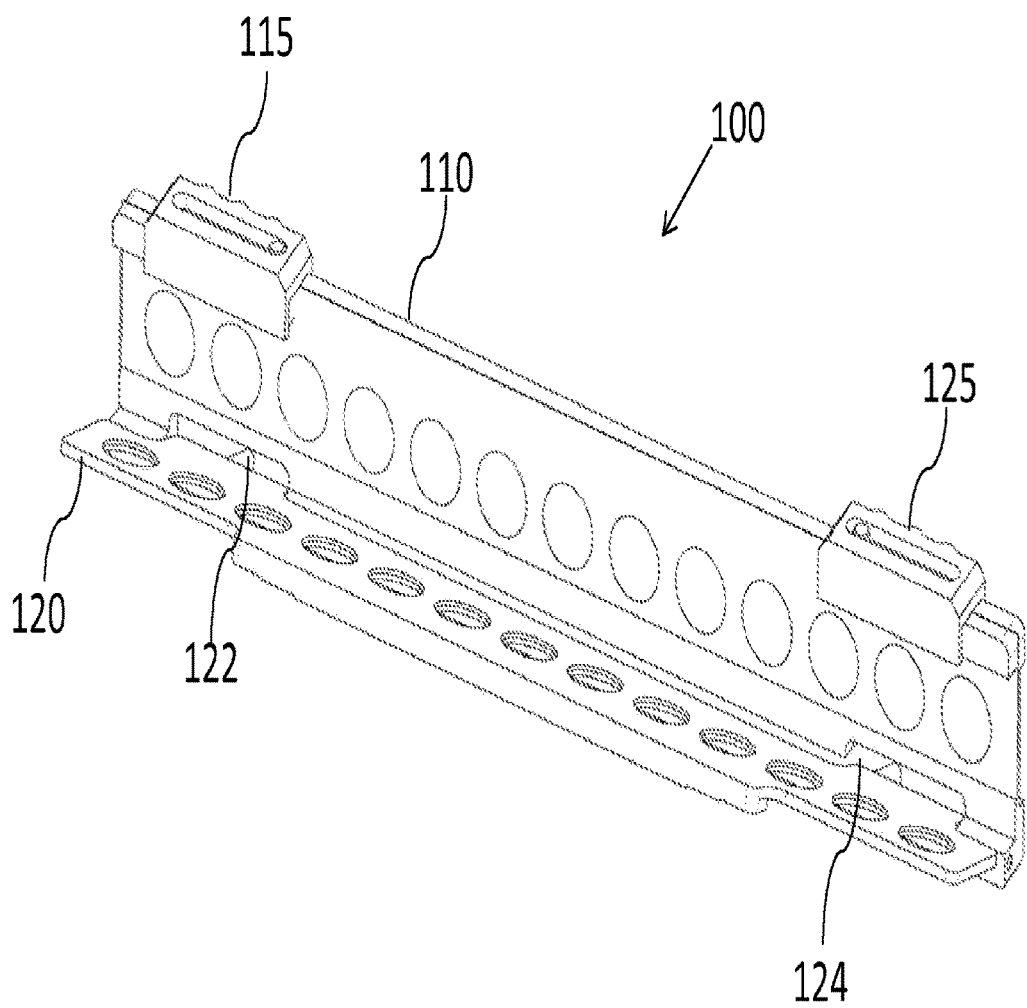
FIG. 1 is an illustration of a sample holder in an open position, in accordance with certain examples.

In certain embodiments, a sample holder configured to retain a sample support for direct sample analysis of a sample on the sample support is shown in FIG. 1. The sample holder 100 comprises a first plate 110 with a retaining device 115. In some examples, the retaining device 115 is generally configured to slide parallel to the longitudinal direction of the plate 110 to engage and disengage a second plate 120. If desired, a second retaining device 125 can be present and configured similar to the sliding device 115 to assist in engagement of the plate 120. In use of the holder 100, the second plate 120 is rotated upward such that the planar surface of the second plate 120 is substantially parallel to the planar surface of the first plate 110. For example, the second plate 120 can be rotatably coupled to the first plate 110 through at least one hinge or joint, such as, for example, joints 122 and 124 to permit rotation of the second plate 120 toward the first plate 110. The sample holder 100 can be designed to position a sample support effective to retain a sample, for at least some period, to permit analysis of the sample, e.g., using direct sample analysis.

In certain examples, the retaining devices 115, 125 can be configured to slide medially to engage the second plate 120 to the first plate 110 or slide laterally to disengage the second plate 120 from the first plate 110. In a typical configuration, a user would slide the retaining devices 115, 125 laterally to disengage the second plate 120 from the first plate 110. A sample support such as, for example, a mesh, a screen or combinations thereof would be placed between the plates 110 and 120. Sample may be loaded onto the sample support prior to placement of the sample support between the plates 110, 120, or sample may be loaded onto the sample support after placement of the sample support in the holder 100 and engagement of the second plate 120 to the first plate 110.

Figure 2:
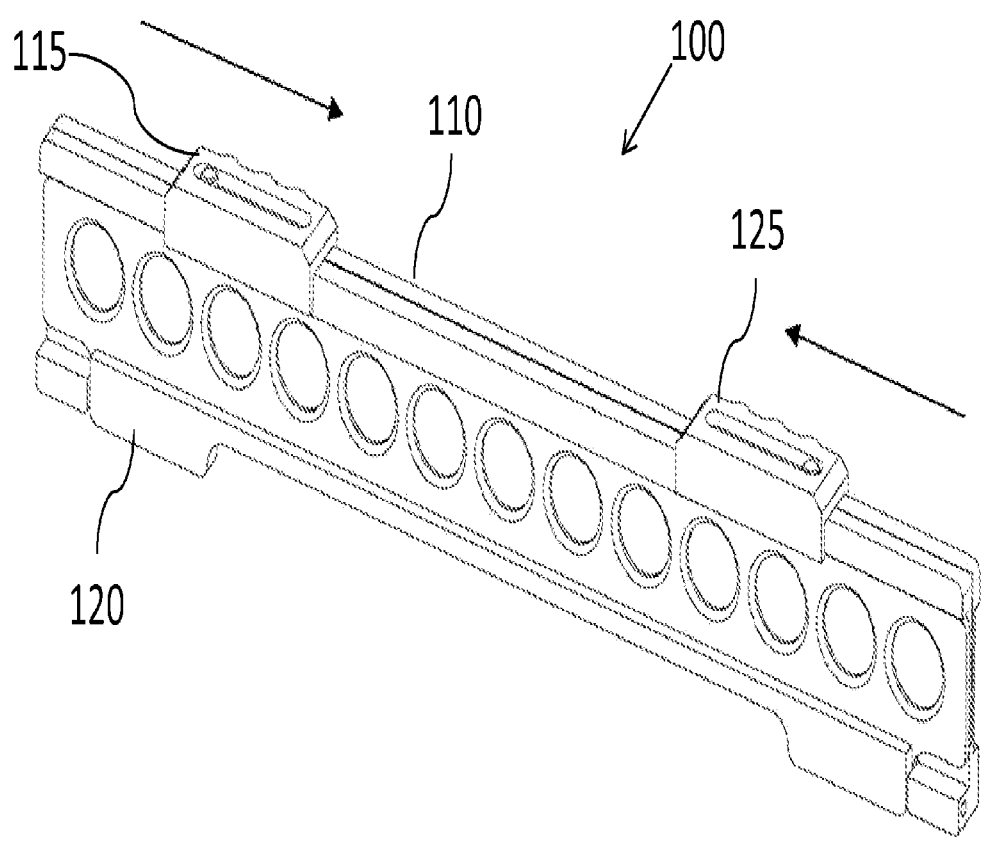
FIG. 2 is an illustration of the sample holder of FIG. 1 in a closed position, in accordance with certain examples.

In certain embodiments, FIG. 2 is an illustration of the second plate 120 being engaged to the first plate 110. The retaining devices 115 and 125 have been moved medially in the direction of the bold arrows shown in FIG. 2. Movement of the retaining devices 115, 125 operates to engage an upper planar surface of the second plate 120 to retain the second plate 120 in the general position shown in FIG. 2. In particular, the second plate 120 can be configured with a suitable geometry such that a portion of the second plate 120 is positioned within the retaining devices 115, 125 to capture the second plate 120 when the retaining devices 115, 125 are in the medial position. Retention of the second plate 120 by the retaining devices 115, 125 acts to retain or sandwich the sample support (not shown) between the first plate 110 and the second plate 120. To disengage the second plate 120 from the first plate 110, the retaining devices 115, 125 are moved laterally toward the ends of the first plate 110. Lateral movement of the retaining devices 115, 125 acts to disengage the upper portion of the second plate 120 from the retaining devices 115, 125 and permit rotation of the second plate 120 downward and away from the first plate 110. This rotation permits a user to remove the sample support and load a new sample support for further analysis of sample.

In certain embodiments, the first and second plates generally include one or more apertures that permit sample on the sample support to be contacted with a fluid, e.g., an ion beam or other fluid that can ionize, atomize, vaporize or otherwise facilitate sampling of the sample on the sample support. In certain examples, the fluid can contact the sample at one side of the sample support, and sample on the sample support can be carried away from the sample holder at an opposite side of the sample holder to a device for analysis, e.g., a mass spectrometer or other suitable devices discussed herein. For example, sample can be ionized using an ion beam that is incident on one side of the sample support, and ionized sample may be ejected and provided to a device fluidically coupled to the sample support. The exact number of apertures present in the sample holder can vary, and each of the first plate and the second plate need not include the same number of apertures. While the illustrations shown in FIGS. 1 and 2 include thirteen apertures in each of the first plate 110 and the second plate 120, this number is not required or limiting. In certain embodiments, the number of apertures in each of the plates of the sample holders described herein may vary from one to about twenty, more particularly from two to about fifteen, for example, about five to about fifteen or about five to about thirteen. Where apertures are present in different rows as described herein, more than twenty apertures may be present. Similarly, the particular geometric shape selected for the apertures need not be circular or even the same one the first plate 110 and the second plate 120. Any geometric shape is possible, including but not limited to, circular shapes, rectangular shapes, triangular shapes, trapezoidal shapes, pentagonal shapes, hexagonal shapes, octagonal shapes and other geometric shapes.

Figure 3:
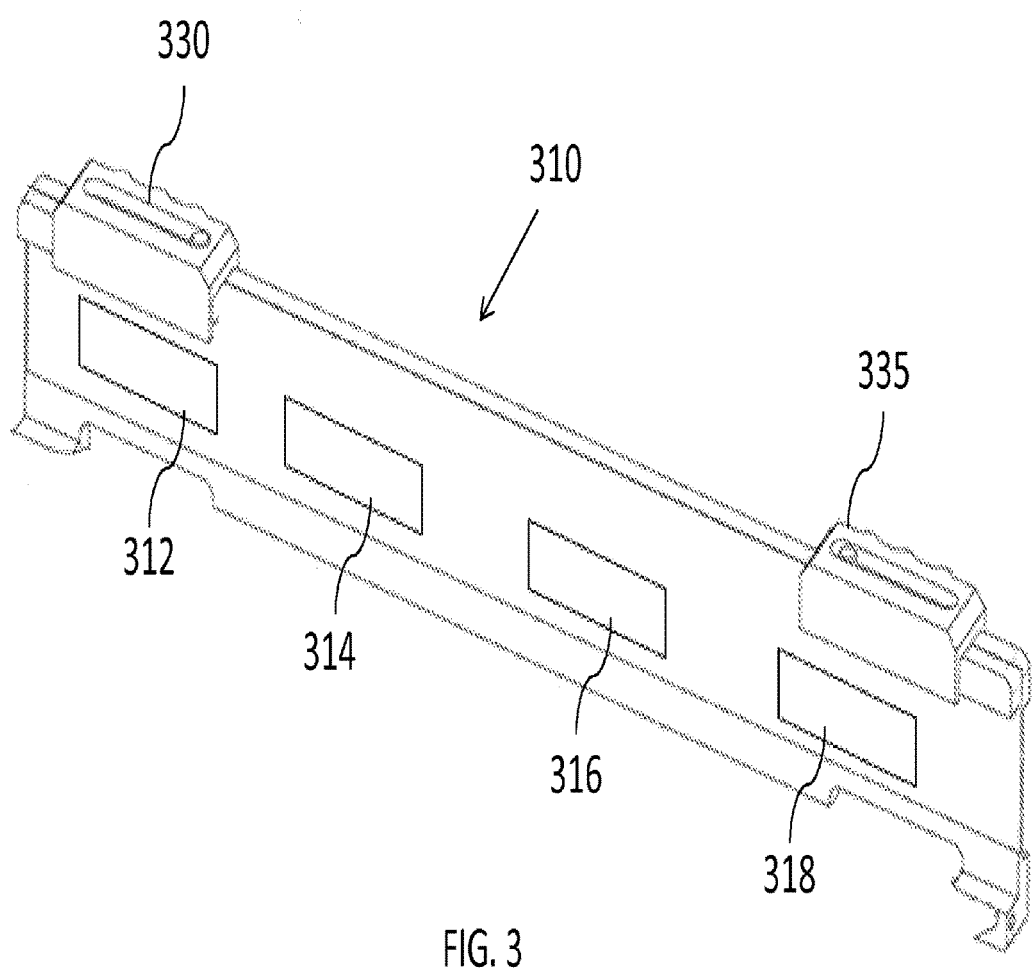
FIG. 3 is an illustration of a plate for use in another sample holder, in accordance with certain examples.
Figure 4:
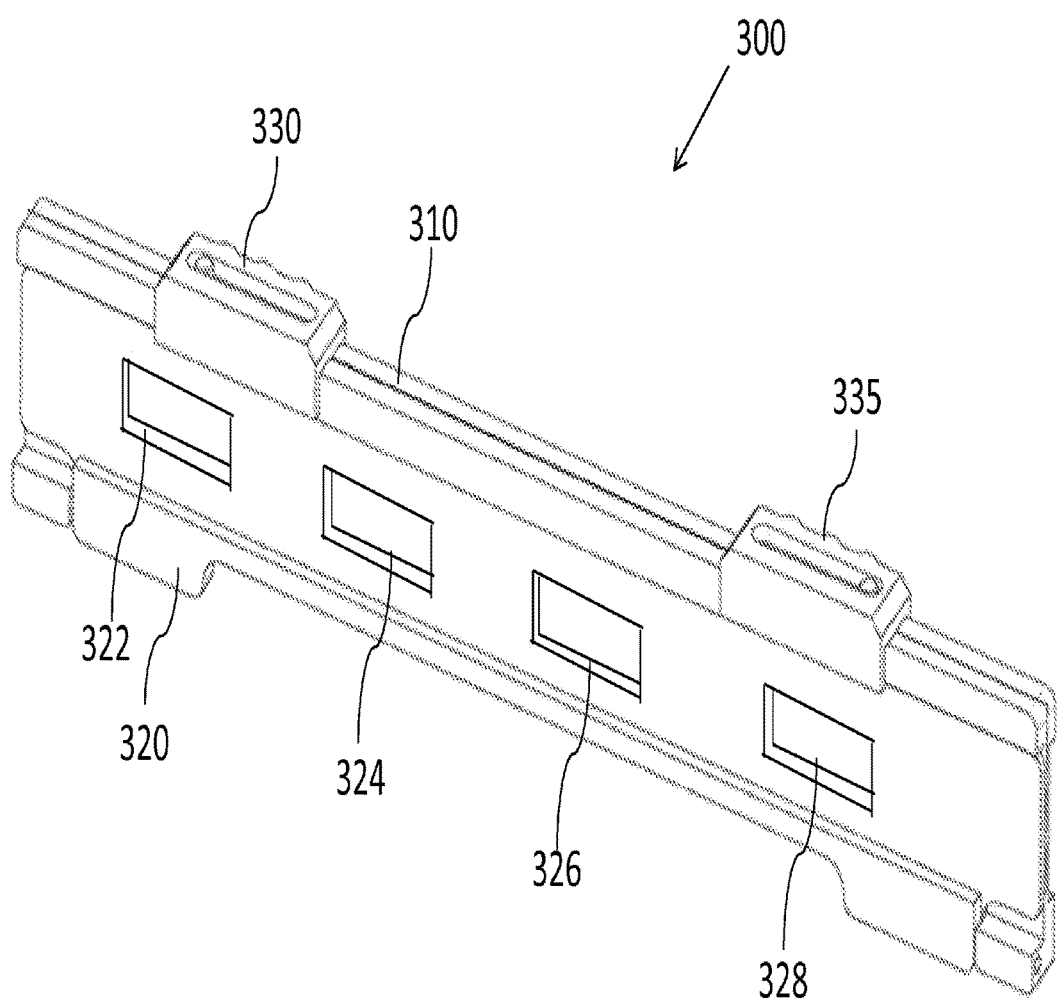
FIG. 4 is an illustration of a sample holder including the plate of FIG. 3, in accordance with certain examples.

In certain examples and referring to FIG. 3, a first plate 310 is shown that comprises four generally rectangular apertures 312, 314, 316 and 318. The first plate 310 also comprises retaining devices 330 and 335 which can function similar to the retaining devices 115, 125. If desired, the second plate (not shown in FIG. 3) can include the same number of apertures as the plate 310 or a different number of apertures as the plate 310. In addition, the apertures of the second plate may have a similar geometry as the apertures of the plate 310 or a different geometry as the geometry of the apertures of the plate 310. In some instances, some of the apertures of the second plate may be sized and arranged similarly to apertures of the first plate 310 and other apertures on the second plate may be sized and arranged differently than apertures of the plate 310. For ease of description, a second plate 320 comprising the same number of apertures as the first plate 310 is shown as being present in FIG. 4. The second plate 320 comprises apertures 322, 324, 326 and 328 which correspond to the openings 312, 214, 316 and 318, respectively, to provide a continuous opening from one side of the sample holder 300 to the other when the second plate 320 is engaged to the first plate 310 using the retaining devices 330, 335. Sample on a sample support (not shown) that is positioned in the apertures 322, 324, 326 and 328 can be contacted with a fluid such as an ion beam to ionize and/or atomize sample for analysis. In some embodiments, the fluid can contact the sample on one side of the holder 300 and ionized sample can exit from an opposite side of the sample holder 300.

Figure 5:
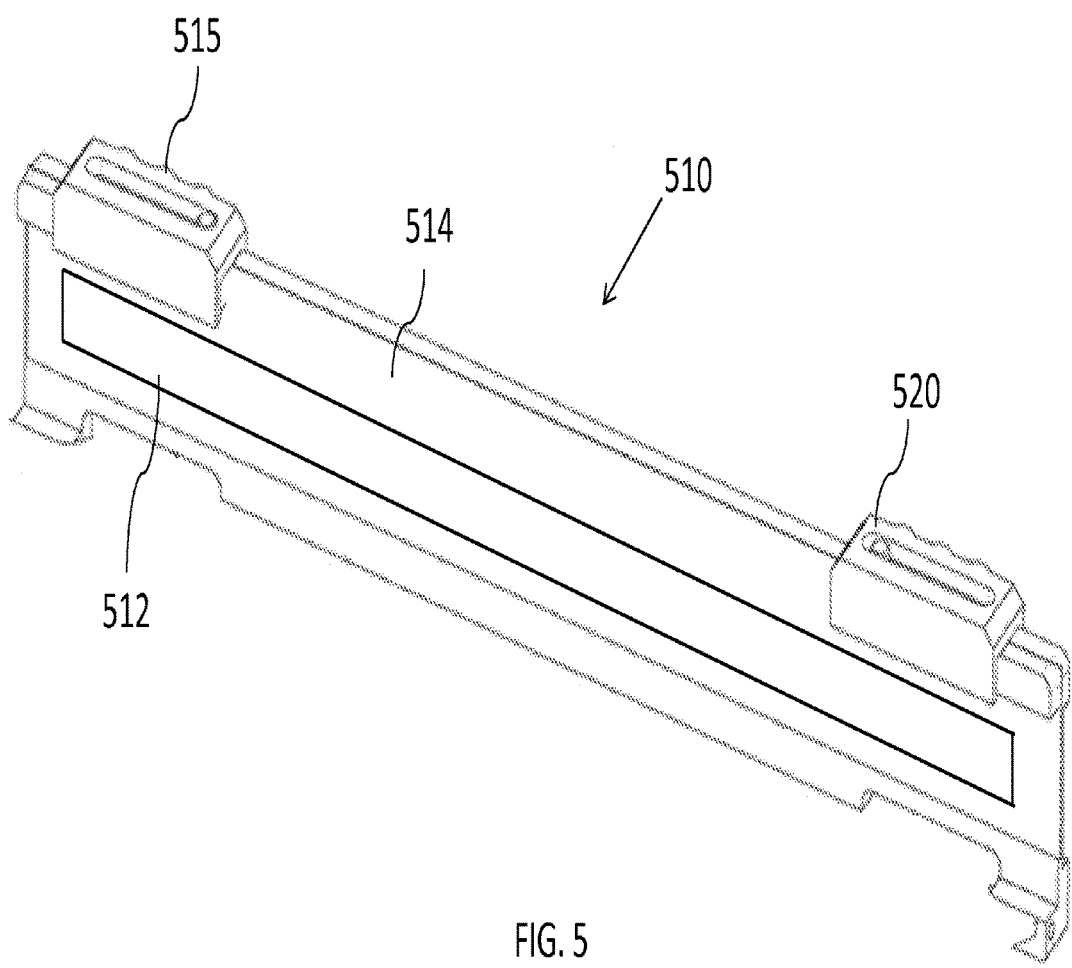
FIG. 5 is an illustration of a plate comprising a single aperture, in accordance with certain examples.

In certain embodiments, one or both of the plates of the sample holders described herein can include a single large aperture and a suitable amount of surface area to retain the sample support in the holder when the two plates are engaged to each other. Referring to FIG. 5, a plate 510 is shown that comprises a single aperture 512 and a frame 514 that is sized and arranged to engage the sample support in a suitable way to retain it within the sample holder. The exact dimensions of the frame 514 and/or dimensions of the opening 512 may vary depending on the particular sample support used with the plate 510. For example, where the sample support is substantially rigid, the opening 512 may be made larger than where the sample support is flexible. Similarly, where the sample support is flexible, it may be desirable to increase the overall dimensions of the frame 514 to deter flexing or bowing of the sample support through the aperture 512.

Figure 6:
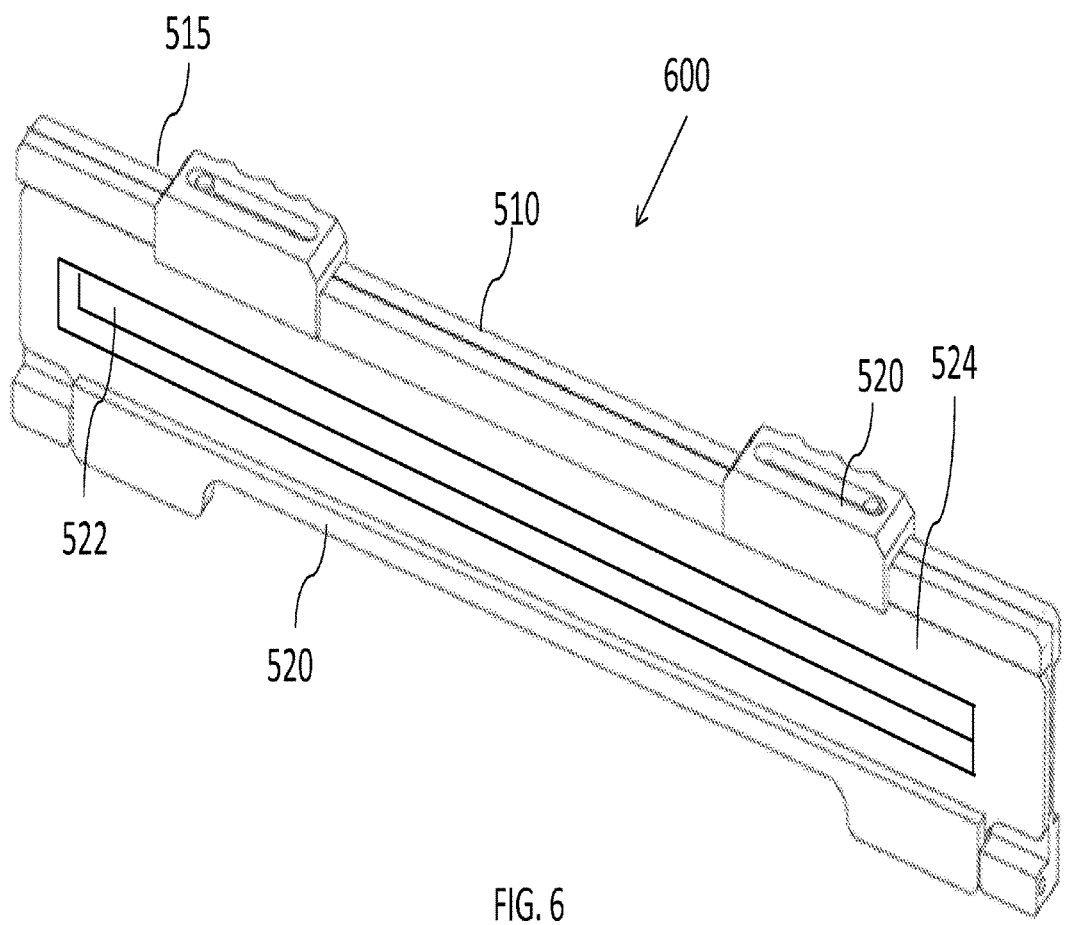
FIG. 6 is an illustration of a sample holder including the plate of FIG. 5, in accordance with certain examples.

In certain examples, the second plate that can couple to the plate 510 may have a different number of apertures such that when the second plate is engaged to the plate 510 using the retaining devices 515 and 520, a side view may appear similar to the view shown in FIG. 2, e.g., where the second plate includes 13 circular apertures, the side view would appear substantially the same as that shown in FIG. 2. If desired however, the second plate may have an aperture sized similar to the aperture 512 shown in FIG. 5. Referring now to FIG. 6, a sample holder 600 is shown that includes a plate 520 coupled to the plate 510. The plate 520 comprises an aperture 522 that is generally sized and arranged similar to aperture 512 of the plate 510. The plate 520 also comprises a frame 524 that can contact some portion of the sample support (not shown) to retain the sample support in the holder 600.

Figure 7A:
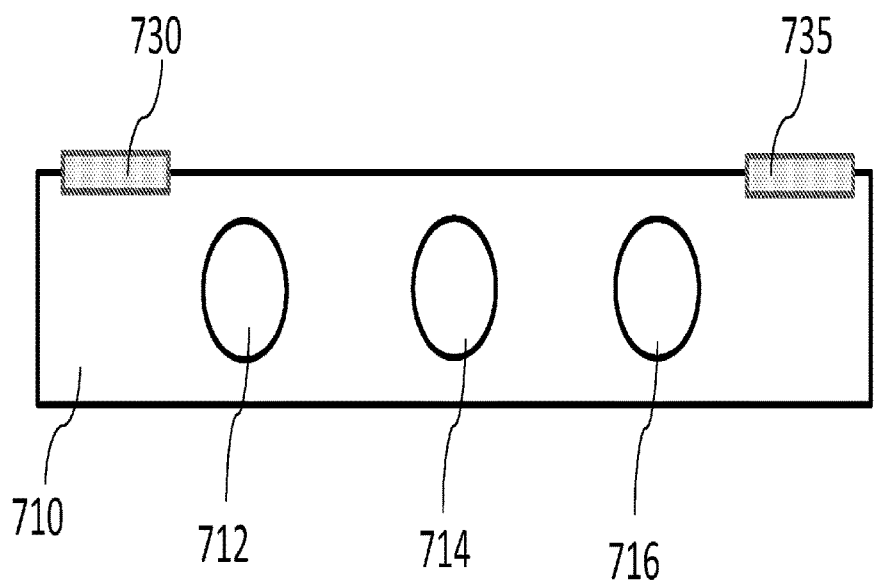
FIGS. 7A-7C are illustrations showing plates that are asymmetric, in accordance with certain examples.
Figure 7B:
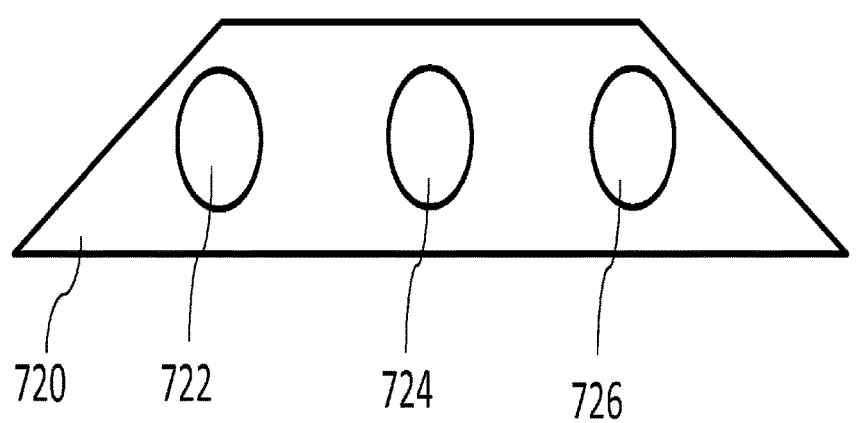
Figure 7C:
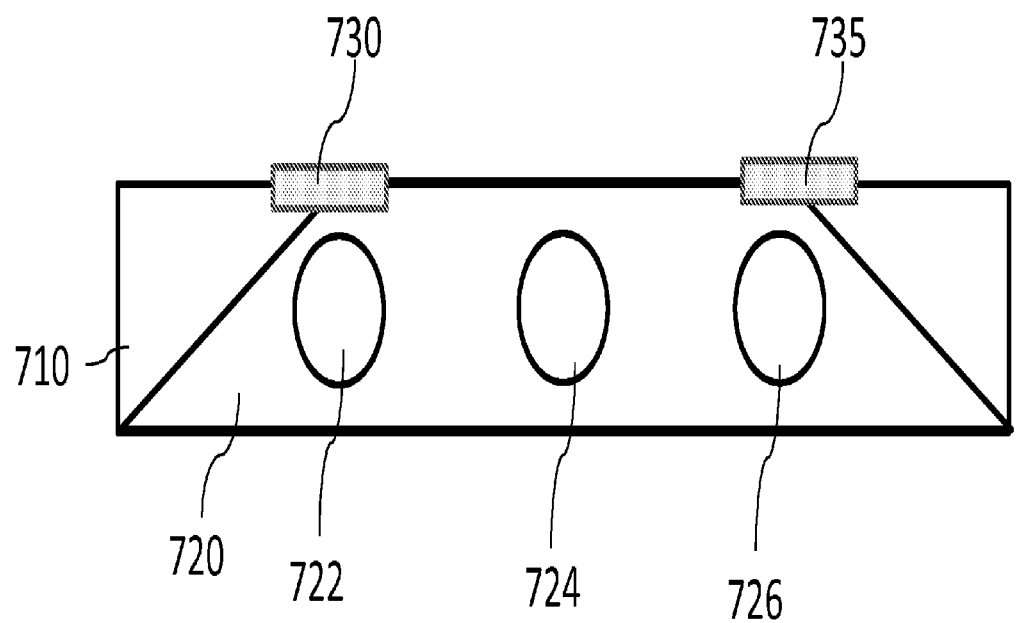

In certain embodiments, the plates of the sample holders described herein may be substantially symmetric or asymmetric. Substantially symmetric plates are shown, for example, in FIGS. 1 and 2. In certain examples, a side view of a first plate 710 is shown in FIG. 7A that is substantially rectangular and comprises apertures 712, 714 and 716 and retaining devices 730 and 735. Referring to FIG. 7B, a second plate 720 comprises a generally trapezoidal shape and apertures 722, 724 and 726 configured to correspond to the apertures 712, 714 and 716, respectively, when the second plate 720 is engaged to the first plate 710. Referring to FIG. 7C, to engage the second plate 720 to the first plate 710, the second plate 720 would be rotated upward until the planar surface of the second plate 720 is substantially parallel to the planar surface of the first plate 710. In some instances, the second plate is rotated until it contacts a sample support between the first plate 710 and the second plate 720. The retaining devices 730, 735 are then moved medially until they capture some portion of the second plate 720. As shown in FIG. 7C, the retaining devices 730, 735 need not make full contact with the second plate 720 but can provide sufficient contact with the plate 720 to hold the plate 720 in a generally upright position.

Figure 8:
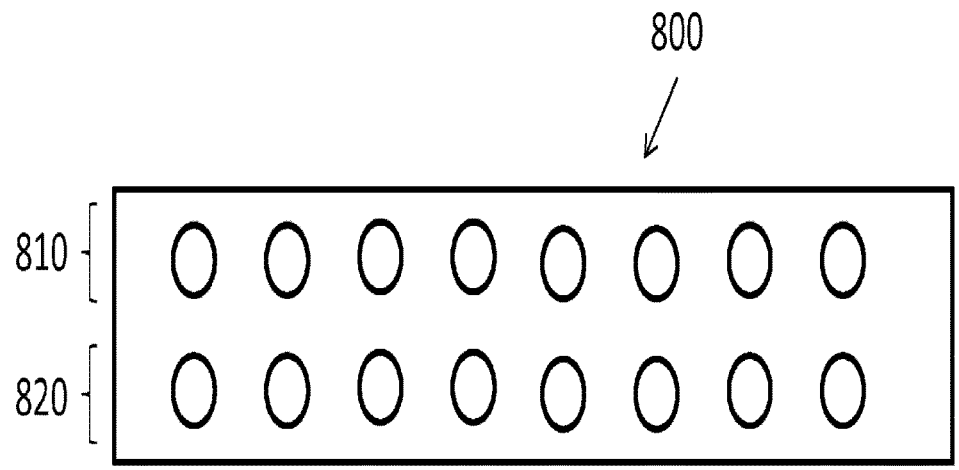
FIG. 8 is an illustration of a sample holder comprising two rows of aligned apertures, in accordance with certain examples.

In some examples, the apertures in the plates can be present in more than a single row or plane to permit loading of a plurality of samples onto the sample support holder. For ease of illustration several examples are described below where the first and second plates include the same number of apertures with substantially similar geometric shapes. It will be recognized by the person of ordinary skill in the art, given the benefit of this disclosure, that the first and second plates may have a different number of apertures. Referring to FIG. 8, a side view of a sample holder 800 is shown comprising two rows 810 and 820 of apertures in each the plate of the sample holder 800. The retaining device has been omitted from FIG. 8 for clarity. In the illustration of FIG. 8, the sample holder 800 include two aligned rows including eight apertures in each row. The number of apertures may be more than eight of fewer than eight as desired, and the geometric shape may also be different than the circular shape shown in FIG. 8. During analysis, all samples may be analyzed in one of the rows 810, 820 followed by analysis of samples in the other row, or samples within the same column may be analyzed followed by analysis of samples in another column. The exact number of rows present in the sample holder 800 can vary and in some examples, two rows, three rows, four rows, five rows or more may be present. Where a plurality of rows are present in the sample holder 800, it may be desirable to reduce the overall size of the apertures to provide a desired center-to-center spacing between different apertures and increases spacing between the apertures to avoid cross-contamination of samples in different apertures.

Figure 9:
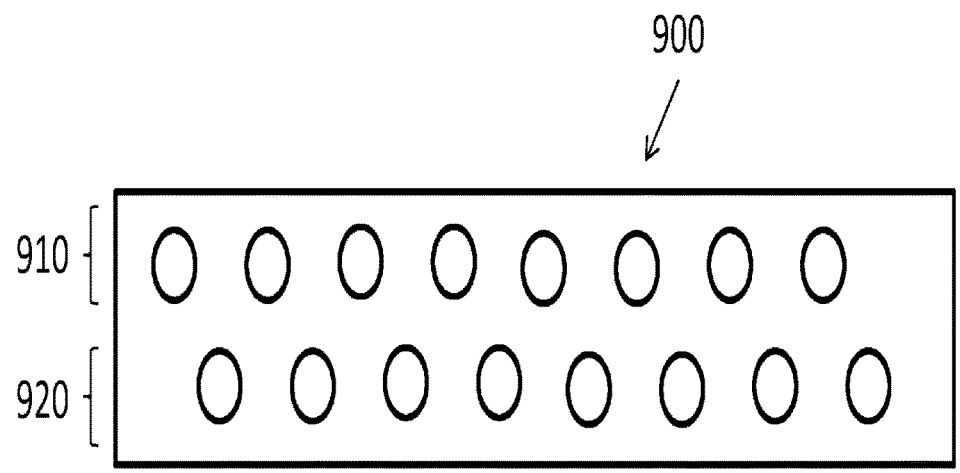
FIG. 9 is an illustration of a sample holder comprising two rows of offset apertures, in accordance with certain examples.

In certain embodiments and referring to FIG. 9, another example of a sample holder 900 is shown. In this illustration, the sample holder 900 includes a first row of apertures 910 and a second row of apertures 920 that are offset from the first row 910. It may be desirable to offset the rows to provide increased spacing between the samples that are loaded on the sample support in the different rows. While the number of apertures shown in the rows 910, 920 are the same, they may be different if desired. The geometric shapes of the apertures of the rows 910, 920 may also be different if desired. During analysis, all samples may be analyzed in one of the rows 910, 920 followed by analysis of samples in the other row, or samples within the same column may be analyzed followed by analysis of samples in another column. The exact number of rows present in the sample holder 900 can vary and in some examples, two rows, three rows, four rows, five rows or more may be present. Where a plurality of rows are present in the sample holder 900, it may be desirable to reduce the overall size of the apertures to provide a desired center-to-center spacing between different apertures and increases spacing between the apertures to avoid cross-contamination of samples in different apertures.

Figure 10A:
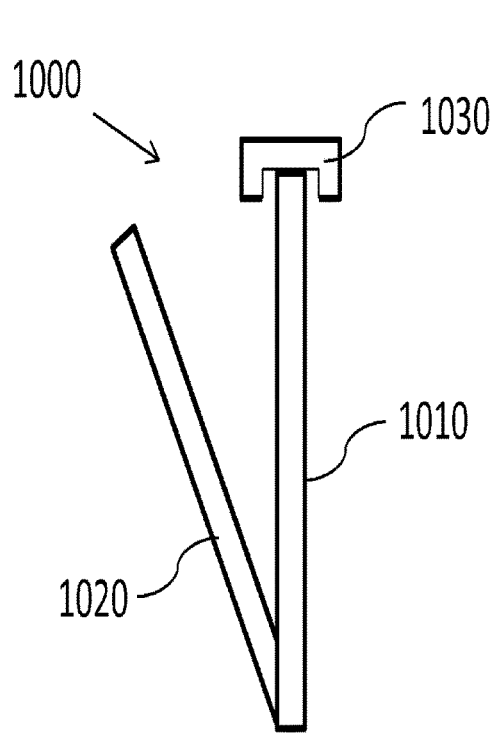
FIGS. 10A and 10B are illustrations showing a side view of a sample holder, in accordance with certain examples.
Figure 10B:
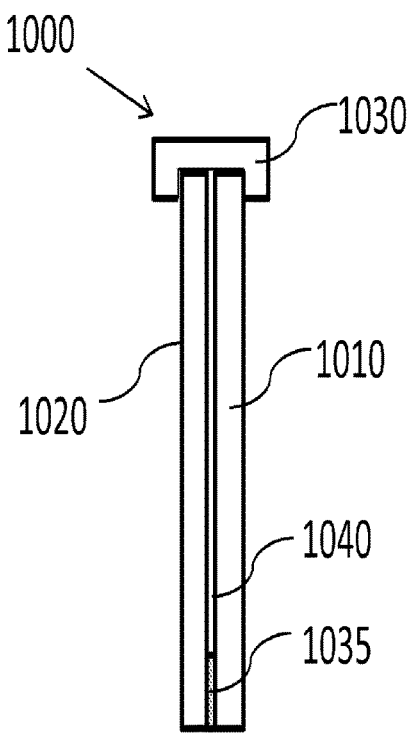

In certain examples, the retaining devices of the sample holders described herein can take many forms including sliding devices, hole and pin devices, e.g., a hole on one plate that can receive a pin on the other plate, a hook on one plate configured to engage a boss or hole on the other plate, a loop on one plate that can engage a boss on the other plate or other fasteners that are effective to retain the first plate and the second plate in an engaged position but permit rapid disengagement of the two plates for sample support loading can be used. In some examples, the retaining devices can be those without any threads on them, e.g., the retaining devices do not use screws or other threaded fasteners to retain engagement of the first plate and the second plate. In other embodiments, the retaining device is effective to function without the use of an external fasteners, e.g., screws, rivets or other fasteners that are separate from the plates. In some embodiments, the retaining device(s) are integral to one of more of the plates, whereas in other embodiments, the retaining devices can be removed from one of the plates to permit cleaning and can then be placed back onto the plate after cleaning for further use. For examples, the retaining device 115 can be snapped into the plate 100 or slid onto the plate 110 from the end of the plate 110 and subsequently removed for cleaning. In some embodiments, the retaining device can be configured as one or more sliding devices as shown in a side view in FIG. 10A. The sample holder 1000 comprises a first plate 1010, a second plate 1020 and a single sliding device 1030 positioned along the upper edge of the plate 1010 and configured to slide along the upper edge in a direction into and out of the figure. As shown in the open position of the sample holder 1000 in FIG. 10A, one position of the sliding device 1030 is configured to permit rotation of the second plate 1020 away from the first plate 1010 to permit sample support loading into the sample holder 1000. A second position of the sliding device 1030 (see FIG. 10B) is effective to engage some portion of the plate 1020 to retain the plate 1020 in a position that is substantially parallel to the plate 1010. A hinge or coupler 1035 permits rotation of the plate 1020 to the upright position shown in FIG. 10B. Once the plate 1020 is rotated upward, the sliding device 1030 can be moved laterally or medially (depending on the exact configuration of the plate 1020) to capture some portion of the plate 1020 and retain it in the upright position shown in FIG. 10B. An open or void space 1040 is created between the plates 1010, 1020 and may be occupied by a sample support.

In certain embodiments, the first plate 1010 can include orthogonal projections or bosses on the surfaces to permit the retaining device 1030 to slide or move between two end points. The first end point may be selected to permit rotation of the second plate 1020 away from the first plate 1010, and the second end point may be selected such that the second plate 1020 will be captured by the retaining device 1030 and held generally parallel to the first plate 1010. In other examples, no bosses or projections are present, and the retaining device 1030 may be slid off the first plate 1010 by sliding it to the end of the plate 1010 and removing it. In other instances, the first plate 1010 can include a longitudinal track or slot that engages a groove on the retaining device 1030 to guide the sliding of the retaining device 1030 back and forth in the longitudinal direction of the first plate 1010.

In examples where the retaining devices take the form other than a sliding device, the first plate 1010 may include a suitable feature that can releasably engage or releasably receive a corresponding feature on the second plate 1020. For example, the sliding device 1030 may be omitted and the second plate 1020 can include a boss that is configured to engage a hole on the first plate 1010 through a friction fit to hold the second plate 1020 to the first plate 1010 for at least some period. In other configurations, the second plate 1020 may include an elastomeric loop that can hook to a feature on the first plate 1010 to retain the first plate 1010 to the second plate 1020. Other retaining devices may also be used to permit engagement of the second plate to the first plate for at least some period.

It will be recognized by the person of ordinary skill in the art, given the benefit of this disclosure that the plates shown in FIGS. 1-10B are merely illustrative of the many different plate configurations that can be used to provide sample holders. Additional components such as gaskets or seals can be present between the plates of the sample holders to provide a tight fit of the sample support in the holder. Where gaskets are present, they may include a substantially inert material, e.g., PEEK, such that unwanted interfering species are not produced during sample analysis. The gaskets may be selected to provide for increased or decreased spacing between the plates to account for differences in thickness for different sample supports. In some embodiments, one or more of the plates may include an alignment device or mechanism configured to align or position the sample support between the plates. In one embodiment, the alignment mechanism may take the form of grooves on the lateral sides of one or more of the plates. In certain examples, the grooves can be designed to rest against one or more edges of the sample support to assist in positioning the sample support in the sample holder. In other embodiments, the alignment mechanism may be a slot on one of the plates of between one of the plates. In certain embodiments, the alignment mechanism may be a track in one or both of the plates that can receive some portion of the bottom edge of the sample support to generally hold the sample support upright while the plates are engaged to each other. Other alignment mechanisms to facilitate insertion of the sample support into the sample holder will be readily selected by the person of ordinary skill in the art, given the benefit of this disclosure. In some examples, the sample holders described herein can include posts or suitable couplings to couple the sample holder to a platform or other structure of the system. If desired, the sample holder can be electrically grounded to prevent unwanted build-up of an electrical charge on the surfaces of the sample holder during analysis. In some embodiments, the exact spacing of the apertures of the plates can vary from about 0.25 inches to about 0.75 inches, though the spacing may be smaller where rows of apertures or present or may be larger where only a few apertures are present.

In certain embodiments, the hinge, joint or coupler that rotatably couples the first plate and the second plate to each other can vary. In some embodiments, the first plate can include a sleeve that is designed to receive a groove on the second plate through a friction fit. In other embodiments, the first and second plates can be coupled to each other by inserting a pin through hinges in each of the first and second plate, e.g., the plates may be coupled in a similar manner as a door is coupled to a door frame by aligning circular openings of the first plate and the second plate and placing a pin through the aligned openings. In other embodiments, one of the plates may comprise a ball and the other may comprise a socket to facilitate the rotatable coupling of the first plate to the second plate. In some examples, the first and second plates are permanently rotatably coupled such that they cannot be separated by manual force without first removing a fastener such as a pin. In other embodiments, the second plate may be designed to be removed from the first plate entirely be manual force to separate the plates at the joint where the plates are coupled. Additional configurations for rotatably coupling the plates will be readily selected by the person of ordinary skill in the art, given the benefit of this disclosure.

In certain embodiments, the sample holders described herein can generally be used with a sample support that is effective to receive a sample and retain the sample for at least some period. The sample support can include many different configurations, shapes, materials, etc. and may be sized and arranged such that it can be sandwiched or otherwise retained between the plates of the sample holders described herein. In some embodiments, the sample support may take the form of a mesh with an effective pore size to retain the sample on the sample support. The pore size and configuration may be selected depending on the form of the sample to be loaded, e.g., liquid, solid, gas, supercritical fluid, etc. While the exact material of the sample support may vary, the sample support typically includes, or is made of, a substantially inert material so no interferences are created from the sample support material leaching or otherwise desorbing from the sample support. In some examples, the sample support can include substantially inert meshes such as, for example, stainless steel meshes, inert polymeric meshes, substantially inert membranes or membrane materials or combinations of any of them.

In a typical sampling operation, the sample can be added to the sample support, e.g., either directly or by suspending the sample in a liquid or dissolving the sample in a solvent, where it is retained at least for a sufficient period to permit analysis of the sample. Where the sample is a solid, it may be crushed, pulverized, homogenized or otherwise rendered into powder or crystalline form to be loaded onto the sample support. A diluent or carrier can be added to the powder to clump or agglomerate the powder to facilitate loading onto the sample support. Where diluents or carriers are used, suitable materials are selected so they do not create species that may interfere with any analysis of the sample. Where the sample is a liquid, it may be sprayed on, dropped on, pipetted on or otherwise introduced onto the sample support. In some embodiments, the sample support can be dipped into a liquid or liquids to load the samples onto the sample support. For example, the sample support can be configured with individual sections that are separated by openings and configured to be dipped or disposed into an individual receptacle, e.g., an individual microwell, to permit dipping of the sample support into a plurality of wells in a microwell plate. Such sample supports would permit automated sample loading and decrease the overall time needed to load samples onto the sample support.

In certain embodiments, the sample support can first be placed in the sample holder described herein and then sample may be loaded onto portion of the sample support that are exposed through the apertures of the sample holder. The sample holder with loaded samples is then placed into an instrument for analysis. In other embodiments, the second plate may include an integral sample support that permits loading of sample onto the integral sample support, rotatable coupling of the second plate and the first plate, engagement of the second plate by a retaining device of the first plate and subsequent analysis of sample on the integral sample support. After sampling, the second plate can be removed, cleaned and reused or it may be discarded and replaced with an additional second plate comprising an integral sample support. It will be recognized by the person of ordinary skill in the art, given the benefit of this disclosure, that the first plate may instead include an integral sample support or both the first plate and the second plates can include integral sample supports.

In some examples, the sample support can be used with a loader which can take the form of a frame or template that mirrors the aperture spacing and size of the plates or plates of the sample holder. The sample support may be placed under the template or sandwiched between the template, and samples can be loaded on the apertures of the template. If desired, the entire sample support plus template can be loaded into the sample holder or the sample support can be separated from the template and then loaded into the sample holder. Where the template is loaded into the sample holder, the template can be produced using similar materials as those used to produce the plates or other components of the sample holders described herein.

In certain embodiments, the plates, retaining devices and other components of the sample holders described herein can be produced using one or more suitable materials that are generally inert so as to not substantially interfere with, or contaminate, any sample analysis. In some embodiments, the materials may be one or more plastic materials including thermoplastics and thermosets. In some embodiments, the plastic material desirably has a melting temperature of greater than 250 degrees Celsius, more particularly greater than 300 degrees Celsius. In certain embodiments, any one or more of the plates, retaining devices, joints, etc., of the sample holders described herein can include a thermoplastic comprising an acrylic polymer, a fluoroplastic polymer, a polyoxymethylene polymer, a polyacrylate polymer, a polycarbonate polymer, a polyethylene terephthalate polymer, a polyester polymer, a polyetheretherketone polymer, a polyamide polymer, a polyimide polymer, a polyamide-imide polymer, a polyaryletherketone polymer or combinations and copolymers thereof. If desired metallic or conductive particles can be included in the thermoplastic to facilitate electrical coupling of the sample holder to an electrical ground. In some embodiments, the thermoplastic used is substantially transparent when viewed with the human eye to facilitate, for example, positioning of the sample support in the sample holder. In certain embodiments, the components of the sample holders can be produced using one or more substantially inert metal materials including, for example, Inconel® alloys, titanium and titanium alloys, aluminum and aluminum alloys, stainless steels, refractories or other suitable materials that include metals and which are substantially inert in the use environment of the sample holder.

In certain embodiments, some components of the sample holder can be produced using materials other than inert materials if desired. For example, the hinges where the plates rotatably couple to each other may generally be out of the fluid stream that contacts the sample and can be produced using materials other than non-inert materials. If desired, the plates can be produced using one inert material and the retaining device can be produced using a different inert material. In some embodiments, the first plate and the second plate can be produced using the same materials or different materials. In other embodiments, different portions of a particular plate can be produced using different materials.

In some embodiments, the components of the sample holders described herein can include a material that can withstand a cleaning operation such as, for example, sonication, solvent washes or other cleaners can be used to clean and/or remove any residue from the sample holder prior to reuse. In some configurations, the materials of the sample holders can withstand such washing steps and substantially no deterioration occurs after washing.

In some examples, the plates can include an indicator material that is designed to change color or otherwise provide a visual indication that the plate has been used before or has exceeded its useful lifetime. The inclusion of visual indicators may be particularly desirable where the sample holders are designed for a single use to permit cross-contamination between samples on different sample supports. In some embodiments, the indicator may be a temperature indicator that can change color after exposure to high temperatures. In other embodiments, the indicator may be an electrical or magnetic indicator, e.g., liquid crystals, that can alter the overall color or optical properties of the sample holder once it has been exposed to an electrical field, magnetic field or other electrical or magnetic stimulus.

Figure 11:
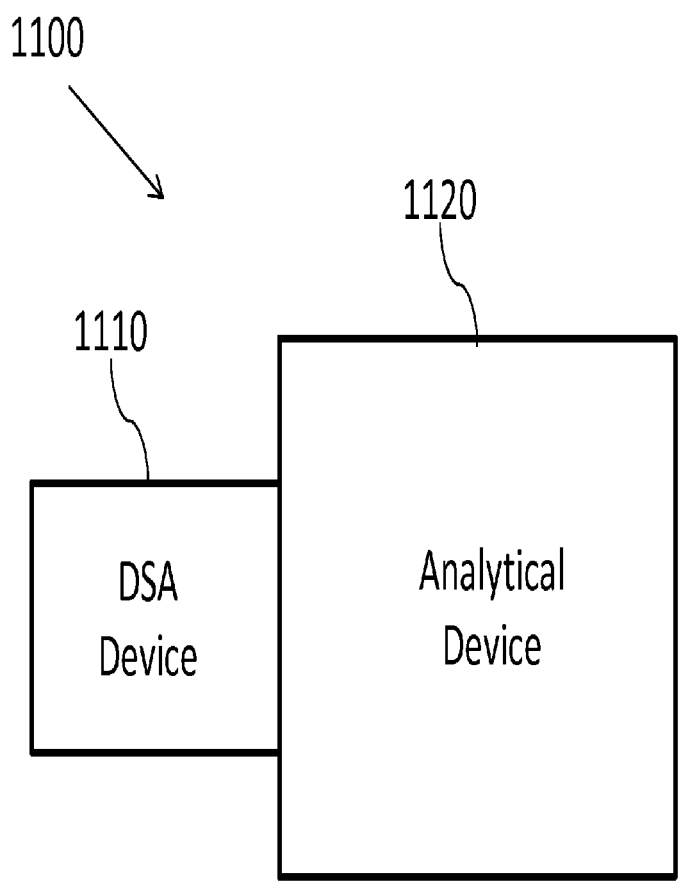
FIG. 11 is an example of a system that include a direct sample analysis device, in accordance with certain examples.

In some examples, the sample holders described herein may be used to permit direct sample analysis of a sample on the sample support loaded into the sample holder. An illustration of a system including a direct sample analysis device is shown in FIG. 11. The system 1100 generally comprises a direct sample analysis (DSA) device 1110 fluidically coupled to an analytical device 1120. In certain embodiments, the analytical device 1120 may take many forms including mass spectrometers, optical absorbance or emission detectors, plasma based analytical systems or other systems. In direct sample analysis, the sample can be directly analyzed without undergoing pre-sample preparation or purification, e.g., without being subjected to one or more purification steps, chromatographic separation steps or the like. In a typical operation, the sample is ionized after collision with an energized ion or atom, e.g., an electronically excited ion or atom. The collisional atoms are typically provided by an ion source such as, for example, an electron ionization source, a chemical ionization source, an electrospray ionization source, an atmospheric-pressure chemical ionization source, a plasma (e.g., inductively coupled plasma), glow discharge sources, field desorption sources, fast atom bombardment sources, thermospray sources, desorption/ionization on silicon sources, secondary ion mass spectrometry sources, spark ionization sources, thermal ionization sources, ion attachment ionization sources, photoionization or other suitable ion sources. Energy transfer can occur between excited molecules from the ion source and the sample which can cause ejection of charged sample species from the sample support. The ejected species may be provided to the analytical device 1120 or system, e.g., a mass analyzer, for detection. In a typical setup, the ions which are provided to the analytical device 1120 pass through an interface (not shown) which may include one or more ion guides or lenses to select an analyte of a desired mass-to-charge ratio and/or remove any interfering or unwanted species.

In certain embodiments where the analytical device 1120 takes the form of a mass spectrometer, many different types of mass analyzers can be used with the sample support holders described herein. For example, sector field mass analyzers, time of flight mass analyzers, quadrupole mass filters, ion traps, linear quadrupole ion traps, orbitraps or cyclotrons, e.g., Fourier transform ion cyclotron resonance or other suitable mass analyzers can be used. As selected ions exit the mass analyzer they can be provided to a detector to detect a change in charge or a current that is produced as the ions impact or travel by a surface, for example. Illustrative detectors include, but are not limited to, electron multipliers, Faraday cups, ion-to-photon detectors, microchannel plate detectors, an inductive detector or other suitable detectors may be used. The mass spectrometer typically will include a display that can provide a spectrum for review by the user. While not described, the mass spectrometer typically would include numerous other components including a vacuum system, one or more interfaces and many other components commonly found in mass spectrometers in use.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A method of loading a sample for direct sample analysis, the method comprising providing a sample holder comprising a first plate configured to permit a sample on a sample support to be contacted by fluid for direct sample analysis, the first plate comprising a retaining device and a plurality of apertures, and a second plate rotatably coupled to the first plate and comprising a same number of apertures as the plurality of apertures of the first plate, the second plate configured to rotate about a longitudinal axis of the second plate to engage the first plate and retain the sample support between the first plate and the second plate, in which the retaining device of the first plate engages the second plate in a first position to retain the sample support between the first plate and the second plate and disengages the second plate in a second position to permit removal of the sample support from the sample holder, in which the apertures of the first plate and the second plate comprise a same size and geometry, and wherein when the first plate is engaged to the second plate in the first position the apertures of the first plate align with the apertures of the second plate.

2. The method of claim 1, further comprising providing instructions for loading the sample on the sample support.

3. The method of claim 1, further comprising providing instructions for inserting the sample support into the sample holder.

4. The method of claim 1, further comprising providing a sample support.

5. The method of claim 1, further comprising providing instructions for analyzing the sample on the sample support using direct sample analysis.

6. A method of loading a sample for direct sample analysis, the method comprising providing a sample holder configured to retain a sample support for direct sample analysis of a sample on the sample support, the sample holder comprising a first plate attached to a second plate through at least one joint, wherein the second plate is configured to rotate about a longitudinal axis of the second plate, the first plate comprising a sliding device configured to hold the second plate towards the first plate in a first position and to permit rotation of the second plate away from the first plate in the second position, in which the holding of the second plate towards the first plate retains the sample support between the first plate and the second plate, in which the first plate comprises a plurality of apertures and the second plate comprises a same number of apertures as the plurality of apertures of the first plate, wherein the apertures of the first plate and the second plate comprise a same size and geometry, and wherein when the first plate is held towards the second plate in the first position the apertures of the first plate align with the apertures of the second plate.

7. The method of claim 6, further comprising providing instructions for loading the sample on the sample support.

8. The method of claim 6, further comprising providing instructions for inserting the sample support into the sample holder.

9. The method of claim 6, further comprising providing a sample support.

10. The method of claim 6, further comprising providing instructions for analyzing the sample on the sample support using direct sample analysis.

11. A method of loading a sample for direct sample analysis, the method comprising providing a sample holder comprising a first plate comprising a plurality of apertures each configured to permit a sample on a sample support to be contacted by fluid for direct sample analysis, the first plate comprising a retaining device, and a second plate comprising an integral sample support and configured to removably couple to the first plate, wherein the second plate comprises a same number of apertures as the plurality of apertures of the first plate, the second plate further configured to rotate about a longitudinal axis of the second plate to engage the first plate, in which the retaining device of the first plate is configured to engage the second plate to the first plate in a first position and to disengage the second plate from the first plate in a second position, and wherein the apertures of the first plate and the second plate comprise a same size and geometry, and wherein when the first plate is engaged to the second plate in the first position the apertures of the first plate align with the apertures of the second plate.

12. The method of claim 11, further comprising providing instructions for loading the sample on the sample support.

13. The method of claim 11, further comprising providing instructions for inserting the sample support into the sample holder.

14. The method of claim 11, further comprising providing a sample support.

15. The method of claim 11, further comprising providing instructions for analyzing the sample on the sample support using direct sample analysis.

* * * * *